(12) United States Patent
Hodorek et al.

(10) Patent No.: US 11,147,542 B2
(45) Date of Patent: Oct. 19, 2021

(54) SURGICAL INSTRUMENT HANDLE WITH IMPLANT SIZING FEATURE AND METHOD OF USING

(71) Applicant: Synthes GmbH, Oberdorf (CH)

(72) Inventors: Brian C. Hodorek, Winona Lake, IN (US); Matt J. Purdy, Winona Lake, IN (US); J. Michael Wiater, Beverly Hills, MI (US); Anand M. Murthi, Baltimore, MD (US); Matthew J. Smith, Columbia, MO (US); Derek J. Cuff, Venice, FL (US); Andrew Jawa, Cambridge, MA (US)

(73) Assignee: Synthes GmbH, Oberdorf (CH)

( * ) Notice: Subject to any disclaimer, the term of this patent is extended or adjusted under 35 U.S.C. 154(b) by 0 days.

(21) Appl. No.: 16/245,191

(22) Filed: Jan. 10, 2019

(65) Prior Publication Data

US 2019/0298322 A1    Oct. 3, 2019

Related U.S. Application Data

(60) Provisional application No. 62/638,240, filed on Mar. 4, 2018.

(51) Int. Cl.
*A61B 17/00* (2006.01)
*A61F 2/46* (2006.01)

(52) U.S. Cl.
CPC ............ *A61B 17/00* (2013.01); *A61F 2/4612* (2013.01); *A61B 2017/0023* (2013.01); *A61F 2/4603* (2013.01); *A61F 2002/4659* (2013.01)

(58) Field of Classification Search
CPC .. A61F 2/4612; A61F 2/4607; A61B 17/1659; A61B 17/1664; A61B 17/1668; A61B 17/1684

(Continued)

(56) References Cited

U.S. PATENT DOCUMENTS

2003/0135275 A1    7/2003    Garcia et al.
2015/0066030 A1    3/2015    McGinley et al.
(Continued)

FOREIGN PATENT DOCUMENTS

EP    3409236 A1    12/2018
WO    96/10962 A1    4/1996
(Continued)

OTHER PUBLICATIONS

"Spaghetti Measuring Tool Plan." Craftsmanspace, www.craftsmanspace.com/free-projects/spaghetti-measuring-tool-plan.html. (Year: 2009).*

*Primary Examiner* — Matthew J Lawson
*Assistant Examiner* — Lisa Nguyen
(74) *Attorney, Agent, or Firm* — BakerHostetler

(57) ABSTRACT

A single-use handle is disclosed for releasably engaging an orthopedic device. The handle includes an elongate body that has a first portion that, in turn, defines a connection end adapted for connection to an upper end portion of a broach. The handle includes a second end portion adapted to be griped by a user. The handle further includes a cylindrical bore at the connection end. The bore is configured to receive a corresponding male portion of a surgical instrument. The handle further includes a button that is adapted to releasably connect the instrument in the bore. The handle further includes a plurality of sizing cavities that have a predetermined size and shape that corresponds to the size and shape of an orthopedic implant. The handle is of a biocompatible, disposable material.

15 Claims, 4 Drawing Sheets

(58) Field of Classification Search
USPC .......................................................... 606/102
See application file for complete search history.

(56) References Cited

U.S. PATENT DOCUMENTS

| | | |
|---|---|---|
| 2017/0156739 A1 | 6/2017 | Nino et al. |
| 2018/0185166 A1* | 7/2018 | Johannaber ............ A61F 2/4612 |
| 2018/0257214 A1* | 9/2018 | Scheuber ............. A61B 17/162 |

FOREIGN PATENT DOCUMENTS

| | | | |
|---|---|---|---|
| WO | 2007/055441 A1 | 5/2007 | |
| WO | 2018/220140 A1 | 12/2018 | |
| WO | WO-2019168987 A1 * | 9/2019 | ......... A61B 17/1613 |

* cited by examiner

SURGICAL INSTRUMENT HANDLE WITH IMPLANT SIZING FEATURE AND METHOD OF USING

BACKGROUND

1. Field of the Invention

The present invention relates generally to orthopedic surgical instruments and, more particularly, to single use orthopedic surgical instruments.

2. Description of the Related Art

At present there exist many thousands of different hand-held surgical tools that are used for performing different procedures on the human or animal body. Typically, each tool has a functional tip that is integrally formed with a handle from metals such as cobalt chrome, stainless steel, or titanium.

Problems with tools of the type currently available include high material and manufacturing costs, as well as significant costs related to sterilizing such devices between surgeries. Disposable or Single use handles are one solution to these problems.

Accordingly, there is a need in the medical field for a disposable handle that may be used with a plurality of surgical devices.

Like other joints and anatomical features of the human body, the elbow joint is complex in its make-up and function. Also, like the other joints and anatomical features of the human body, the elbow joint is unique unto itself and requires specific consideration for its reconstruction or replacement. The complexity and uniqueness of this joint are best appreciated by considering the skeletal motions which are involved in its movement.

In the transition of the hand and forearm from pronation to supination the radius and ulna of the forearm transition from a crossed relationship to a side-by-side relationship. In this movement there is a relative rotation of the radius bone about the ulna. Also, during the transition between pronation and supination there is some relative translational movement between the radius bone and the ulna. The consequence of this is that from a reference point on the ulna, the radius bone appears to move with a general motion that includes both translation and rotation. The head of the radius interacts with the capitellum and the radial notch of the ulna during pronation and supination, providing elbow and forearm stability during rotation and translation.

In addition to its importance as a component of forearm function, the radial head is an equally important component of normal elbow function. Indeed, elbow function involves bending, lifting and twisting movements, all of which require joint stability. Because motions in the human body require the interaction of various anatomical components, it is important that replacement of a component be precise in form, size, and orientation. While the head of the radius bone directly engages the capitellum of the humerus and the radial notch of the ulna, it also relates indirectly to other anatomical components of the arm. Specifically, ligaments surrounding the radial head are essential to elbow stability. Further, misalignment of the radius bone will cause poor radial-capitellar joint contact, leading to subluxation, or poor alignment of the elbow. It follows that the wrist and shoulder joints are also affected by the alignment of the radius bone.

The importance of having a workable prosthesis for the head of the radius bone is underscored by the debilitating effects which commonly result when a joint becomes damaged due to fracture, arthritis, or osteochondrosis. It is well known that radial head resection, as seen in elbow injuries, results in persistent elbow instability. Additionally, forearm axial instability can result from radial head excision if the remaining stabilizers, i.e., the supporting ligaments, are compromised. Because this loss of stability affects the interdependent functions of the elbow and forearm, when the radial head is damaged, it is common to see further damage to other components of the radial-ulnar joint system, including, but not limited to, the complex system of supporting ligaments that encase the elbow joint. It has been well demonstrated that damage to any one of the components of the radial-ulnar joint system leads to pain, weakness, and loss of motion. It is, therefore, of great importance to the patient that damage to the radial head be remedied. As with all surgeries, it is desirable for such procedures to be performed as efficiently (quickly, safely, and accurately) as possible.

Thus, a further need exists, for a device usable during humeral head replacement for a damaged elbow joint.

SUMMARY

In a first exemplary embodiment, the present invention includes a single-use handle for releasably engaging an orthopedic device, said handle comprising: an elongate body, said body having a first portion defining a connection end adapted for connection to the upper end portion of the broach, and a second portion adapted to be gripped by a user; said body further comprising a longitudinal axis, and a cylindrical bore disposed along said longitudinal axis in communication with said connection end; said bore adapted to receive a corresponding male portion of a surgical instrument; a button, said button disposed on the exterior of said body and adapted to selectively and means for releasably connecting said instrument to said bore; a plurality of spherical cavities disposed on the exterior of said body, each cavity of said plurality of cavities having a predetermined size and shape where said shape corresponds to the size and shape of an orthopedic implant, said handle comprising a biocompatible, disposable, material.

BRIEF DESCRIPTION OF THE DRAWINGS

The present invention will be understood more fully from the detailed description given hereinafter and from the accompanying drawings of the preferred embodiment of the present invention, which, however, should not be taken to limit the invention, but are for explanation and understanding only.

In the drawings.

Corresponding reference characters indicate corresponding parts throughout the several views. The exemplary embodiments set forth herein are not to be construed as limiting the scope of the invention in any manner.

DETAILED DESCRIPTION OF THE EMBODIMENTS

The present invention will be discussed hereinafter in detail in terms of various exemplary embodiments according to the present invention with reference to the accompanying drawings. In the following detailed description, numerous specific details are set forth in order to provide a thorough understanding of the present invention. It will be obvious, however, to those skilled in the art that the present invention may be practiced without these specific details. In other instances, well-known structures are not shown in detail in order to avoid unnecessary obscuring of the present invention.

Thus, all of the implementations described below are exemplary implementations provided to enable persons skilled in the art to make or use the embodiments of the disclosure and are not intended to limit the scope of the disclosure, which is defined by the claims. As used herein, the word "exemplary" or "illustrative" means "serving as an example, instance, or illustration." Any implementation described herein as "exemplary" or "illustrative" is not necessarily to be construed as preferred or advantageous over other implementations. Moreover, in the present description, the terms "upper", "lower", "left", "rear", "right", "front", "vertical", "horizontal", and derivatives thereof shall relate to the invention as oriented in FIG. 1.

Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
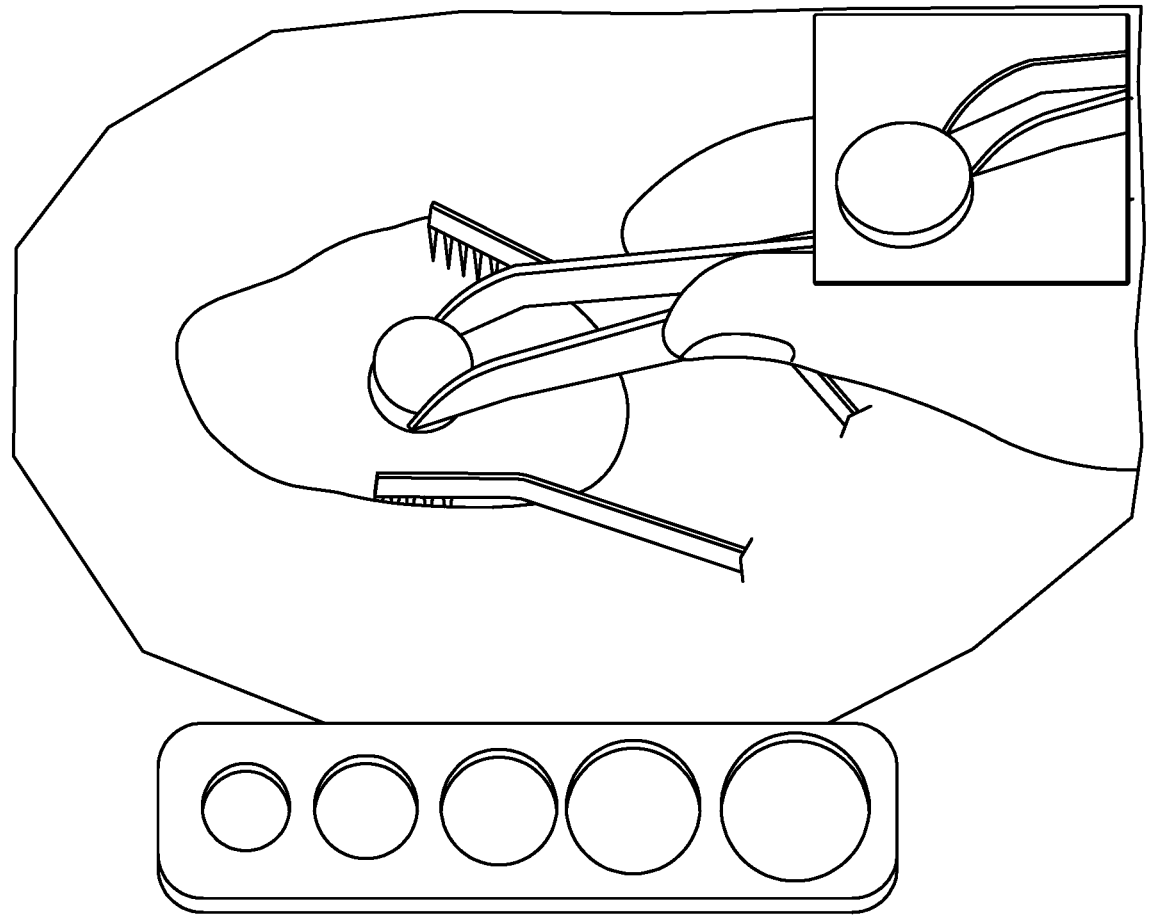
FIG. 1 shows prior art sizing devices.
Figure 2:
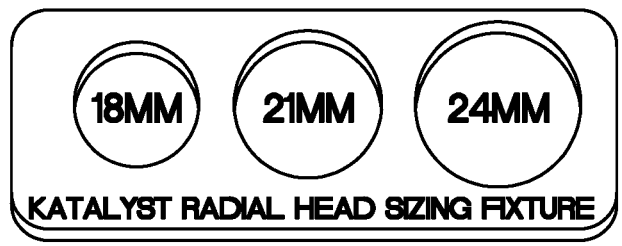
FIG. 2 shows a top view of an apparatus in accordance with an exemplary embodiment of the present invention.
Figure 3:
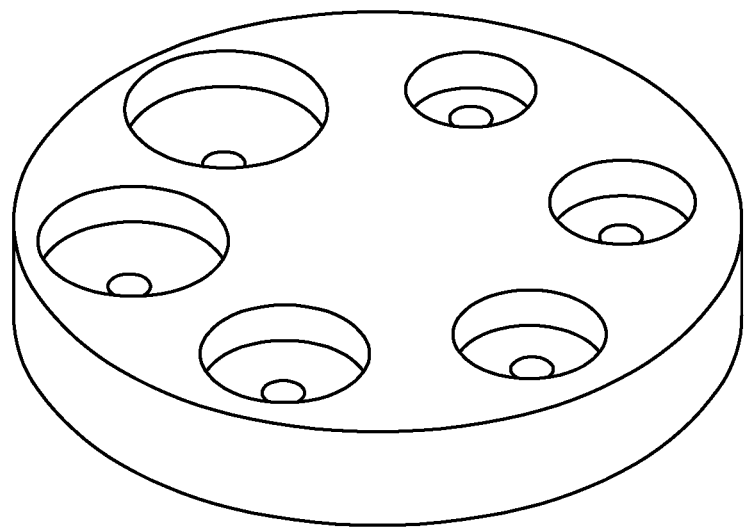
FIG. 3 shows a bottom view of an apparatus in accordance with an exemplary embodiment of the present invention.

Referring now to FIGS. 1-3, there are shown various prior art radial head sizing devices. In current surgical techniques for radial head replacement, surgeons typically use the following steps: (1) performing an initial skin incision; (2) performing an extensor split; (3) resecting the radial neck; (4) reaming the canal; (5) planning the resected surface; (6) rebuilding the fragments in a sizer dish; (6) assembling the trial implant; (7) inserting the trial implant; (8) performing a trial range of motion; (9) removing the trial implant; (10) disassembling and reassembling the trial implant; (11) inserting the trial implant; (12) performing another trial range of motion; (13) removing the trial implant; and (14) inserting the final implant.

Those of skill in the art will appreciate that prior art devices require various instrument sets to remove and reassemble the trial implant. Additionally, a surgeon must use a remote sizing device to determine the appropriate radial head implant size.

Figure 4:
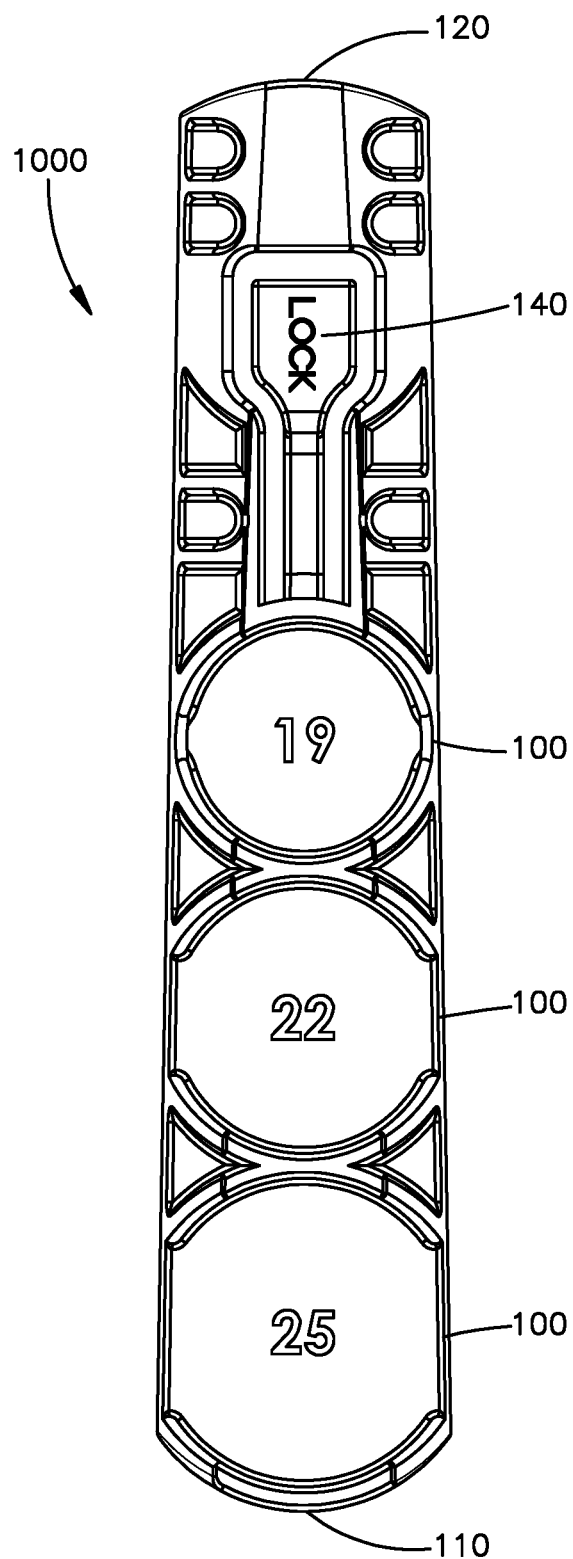
FIG. 4 shows a first end view of an apparatus in accordance with an exemplary embodiment of the present invention.
Figure 5:
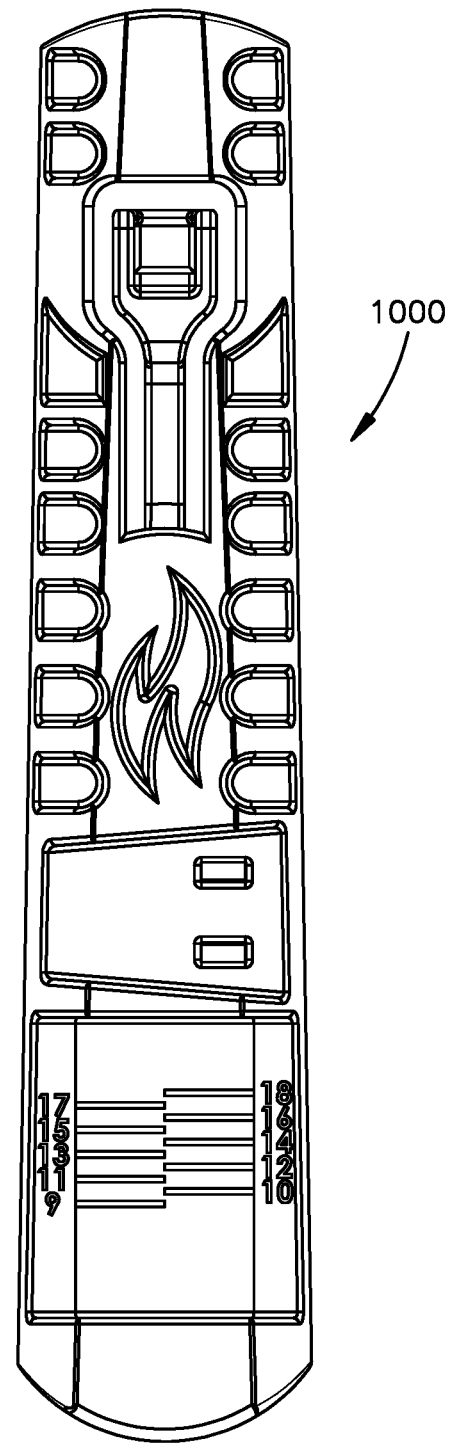
FIG. 5 shows a second end view of an apparatus in accordance with an exemplary embodiment of the present invention.

Referring now to FIGS. 4 and 5, which show, respectively, a top view and a bottom view of handle 1000 in accordance with an exemplary embodiment of the present invention. As illustrated in FIG. 4, handle 1000 comprises an elongate, preferably tapered, body. Handle 1000 further comprises a plurality, preferably at least three, sizing cavities 100. It is preferred to have three or more cavities to reduce the likelihood that a surgeon will have to use a separate device to size the humeral head.

Figure 7:
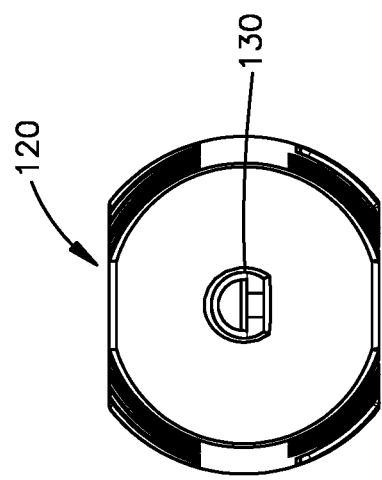
FIG. 7 shows a side view of an apparatus in accordance with an exemplary embodiment of the present invention.
Figure 8:
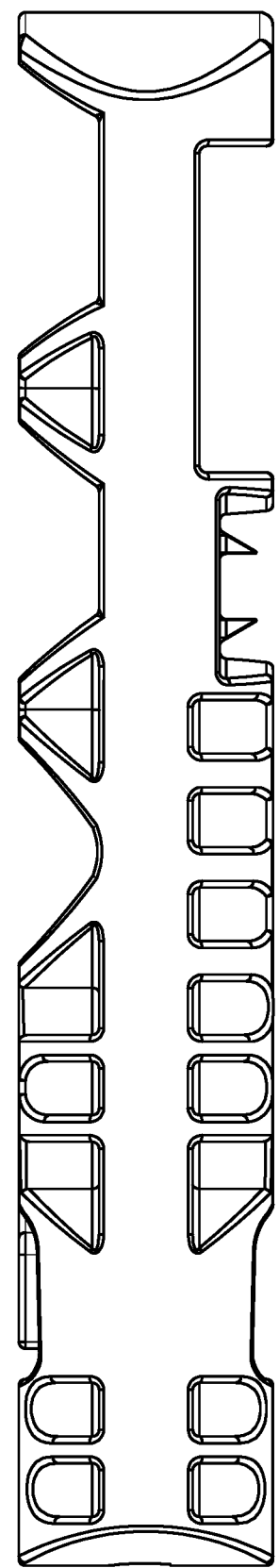
FIG. 8 shows a view of an apparatus in accordance with an exemplary embodiment of the present invention.

Referring still to FIGS. 4-5 as well as to FIG. 7, where there is shown a side view of apparatus 1000, each cavity 100 comprises a unique size and may also comprise a unique shape. However, in the preferred embodiment, each cavity 100 is generally spherical in shape.

Figure 6:
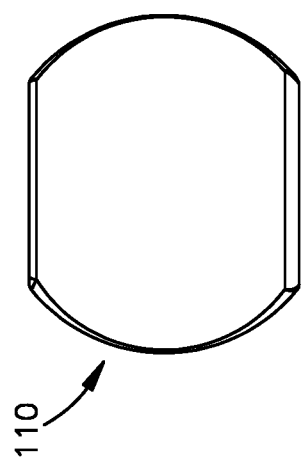
FIG. 6 shows a side view of an apparatus in accordance with an exemplary embodiment of the present invention.

Referring now to FIGS. 6-7, FIG. 6 shows proximal end 110 of handle 1000. FIG. 7 shows opposing distal connecting end 120 of handle 1000. Handle 1000, in one exemplary embodiment, comprises a channel 130 along the longitudinal axis (not shown) of handle 1000 for releasably receiving a corresponding male portion of a surgical device. As shown in FIG. 4, handle 1000 may comprise a button 140 or other quick release mechanisms for engaging such male shaft of a surgical instrument.

Preferably, handle 100 comprises biocompatible, disposable, recyclable materials.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

The invention claimed is:

1. A single-use handle for releasably engaging an orthopedic device, said handle comprising:
   an elongate body, said body having a first portion defining a connection end adapted for connection to an upper end portion of a surgical instrument, and a second portion adapted to be gripped by a user;
   said body further comprising a longitudinal axis, and a cylindrical bore that is disposed along said longitudinal axis and extends into said connection end, said bore adapted to receive a corresponding male portion of the surgical instrument;
   a button adapted to selectively and releasably connect said instrument to said bore;
   a plurality of sizing cavities disposed on an exterior of said body, the sizing cavities each having a different respective predetermined size that corresponds to a respective size and shape of an orthopedic implant.

2. The single-use handle of claim 1, comprising a biocompatible, disposable, material.

3. The single-use handle of claim 1, wherein the sizing cavities comprise three sizing cavities.

4. The single-use handle of claim 3, wherein the sizing cavities decrease in size along a direction from the second portion toward the connection end.

5. The single-use handle of claim 3, wherein the sizing cavities are adjacent each other.

6. The single-use handle of claim 5, wherein a first one of the sizing cavities is disposed at a proximal end of the elongate body.

7. The single-use handle of claim 6, wherein a first wall defines the first one of the sizing cavities, a second wall defines a second one of the sizing cavities, and a third wall defines a third one of the sizing cavities.

8. The single-use handle of claim 7, wherein the first, second, and third walls are generally circular in plan view.

9. The single-use handle of claim 7, wherein the first one of the sizing cavities is a largest cavity of the sizing cavities, the second one of the sizing cavities is smaller than the largest cavity of the sizing cavities, and the third one of the sizing cavities is smaller than the second one of the sizing cavities.

10. The single-use handle of claim 9, wherein respective outer perimeters of the first and second sizing cavities are interrupted by a side wall of the elongate body.

11. The single-use handle of claim 10 wherein the sizing cavities are all substantially spherical.

12. An assembly comprising:
the single-use handle of claim 11; and
the surgical instrument, wherein the surgical instrument comprises a broach.

13. The single-use handle of claim 9, wherein the second one of the sizing cavities is between the first and third ones of the sizing cavities.

14. The single-use handle of claim 1, wherein the button is disposed on the exterior of said body.

15. The single-use handle of claim 1, wherein the predetermined sizes and shapes of the cavities correspond to the size and shape of the orthopedic implant for a radial head of an elbow.

* * * * *